United States Patent [19]
Ambesi Impiobato et al.

[11] Patent Number: 5,935,855
[45] Date of Patent: Aug. 10, 1999

[54] METHOD FOR THE PREPARATION AND CONSERVATION OF CELLULAR CULTURES OR PARTS OF CELLS IN THE READY STATE FOR BIOLOGICAL TESTS

[75] Inventors: Francesco Saverio Ambesi Impiobato, Tricesimo; Alberto Degrassi, Udine; Silvestro Formisano, Ercolano; Stefano Lavaroni, Buttrio, all of Italy

[73] Assignee: Consorzio Di Ricerche Biomediche, Udine, Italy

[21] Appl. No.: 08/930,970

[22] PCT Filed: Apr. 9, 1996

[86] PCT No.: PCT/IB96/00289

§ 371 Date: Feb. 26, 1998

§ 102(e) Date: Feb. 26, 1998

[87] PCT Pub. No.: WO96/32470

PCT Pub. Date: Oct. 17, 1996

[30] Foreign Application Priority Data

Apr. 12, 1995 [IT] Italy ................. UD95A0066

[51] Int. Cl.$^6$ ............... C12N 5/06; C12N 5/08; C12N 5/00
[52] U.S. Cl. ........... 435/353; 435/374; 435/325
[58] Field of Search ............... 435/325, 352, 435/353, 354, 374, 375, 376, 377, 378, 379, 384, 391, 392, 404, 406, 408

[56] References Cited

U.S. PATENT DOCUMENTS

| | | | |
|---|---|---|---|
| 4,608,341 | 8/1986 | Ambesi-Impiombato | 435/353 |
| 4,609,622 | 9/1986 | Kohn et al. | 435/29 |
| 4,795,740 | 1/1989 | Cohen et al. | 514/14 |
| 5,256,571 | 10/1993 | Hurley et al. | 436/17 |

FOREIGN PATENT DOCUMENTS 399647 of 1990 European Pat. Off. .

OTHER PUBLICATIONS

Meyer et al.; "adenylylation state of glutamine synthetase and permeability properties of *Pseudomonas fluorescens*"; Arch Biochem Biophys, May 1, 1986, 246(2) pp. 622–632 (Abstract).

Eraizer et al.; "Characteristics of human embryonic hepatocytes cultivated in vitro"; Exp. Biol. Med., 1975, 79/5 pp. 598–600 (Abstract).

Withers, L.A.; Germplasm preservation through tissue culture: an overview—plant cell culture storage propagation, Dept of Agriculture & Horticulture, Nottingham Univ., pp. 315–341, 1983 (Abstract). Dialog Accession No. 84–08249.

Withers, L.A.; "The Freeze Preservation of Synchronously Dividing Cultured Cells of Acer–Pseudoplatanus"; Cryobiology 15 (1), 1978, pp. 87–82 (Abstract).

Bagchi et al.; "Search for yeast strains suitable for large–scale production of fat: effect of nitrogen deficiency on accumulation and composition of fat in some yeasts—*Rhodotorula glutinis* and Candida sp. etc. isolated from soil"; Chem. Soc. (621,) 1985, pp. 86–87 (Abstract).

Curcio et al. "Long–term culture and functional characterization of follicular cells from adult normal human thyroids," Proc. Natl. Acad. Sci. USA Sep. (1994) 91: 9004–8.

Davies et al. "Functionality of thyroid–stimulating antibodies assessed by cryopreserved human thyroid cell bioassay," J. Clin. Endocrinol. Metab. (1983) 57(5): 1021–27.

Hay, R.J. in "Animal Cell Culture: A Practical Approach", Freshney, R.I., Ed. (1987) (IRL Press: Oxford) p. 71–113.

Takano et al., "Detection Of Thyroid–Stimulating Antibody Using Frozen Stocks Of Chinese Hamster Ovary Cells Transfected With Cloned Human Thyrotropin Receptor", Endocrine Journal, vol. 44, No. 3, 1997, pp. 431–435.

*Primary Examiner*—Jean C. Witz
*Assistant Examiner*—Susan Hanley
*Attorney, Agent, or Firm*—Leydig, Voit & Mayer, Ltd.

[57] ABSTRACT

Method for the preparation and conservation of cellular cultures or parts of cells, whereby the cellular cultures or parts of cells, after having been subjected to a step of starvation (12), undergo a process of conservation (24) without a significant loss of vitality or function and can therefore be supplied in the ready state for biological dosages.

7 Claims, 1 Drawing Sheet

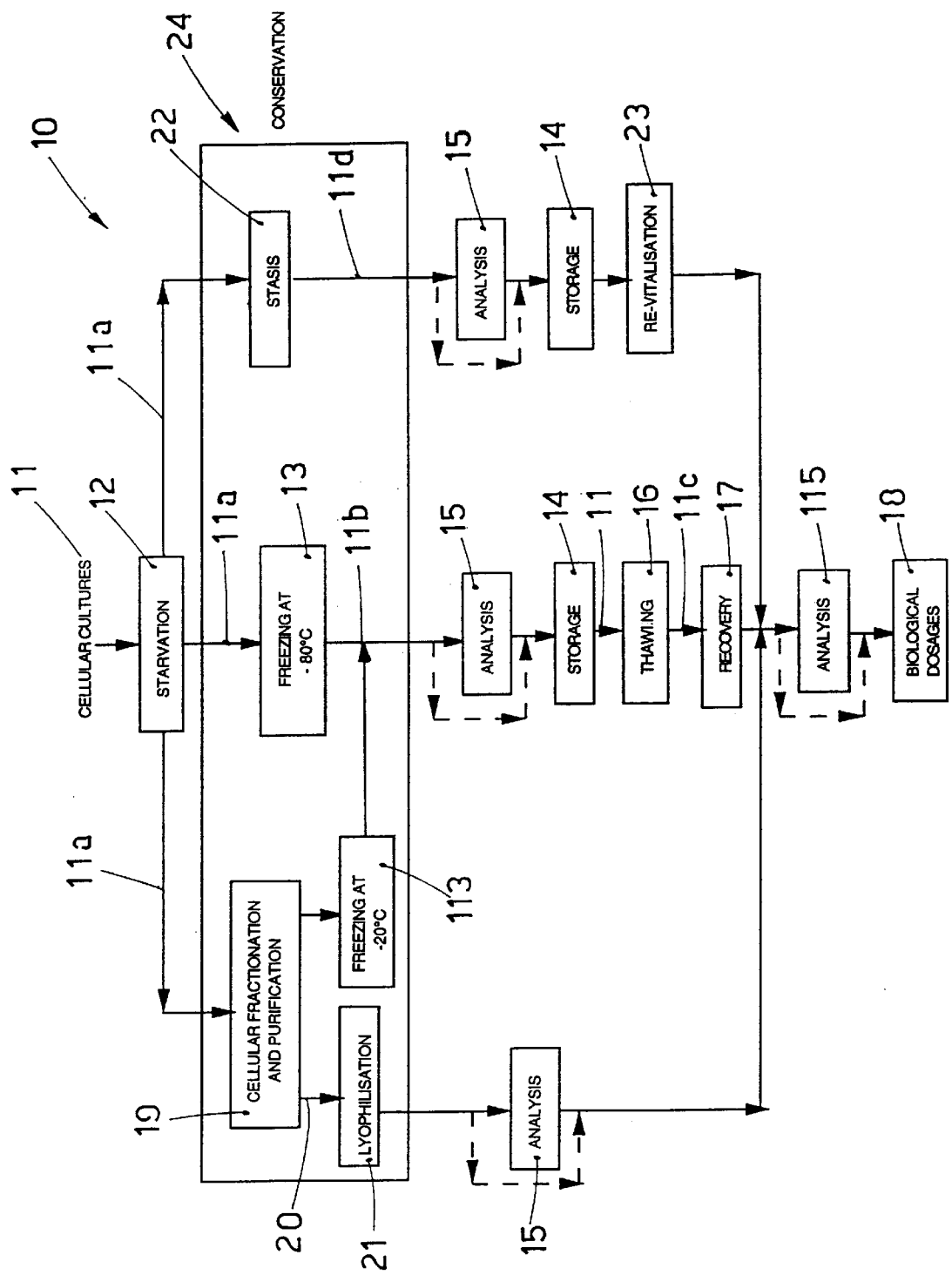

METHOD FOR THE PREPARATION AND CONSERVATION OF CELLULAR CULTURES OR PARTS OF CELLS IN THE READY STATE FOR BIOLOGICAL TESTS

This application is the National Stage of International Application No. PCT/IB 96/00289 filed Apr. 09, 1996.

TECHNICAL FIELD

This invention concerns a method for the preparation and conservation of cellular cultures or parts of cells in the ready state for biological test.

The method according to the invention is employed in the biological, medical and research fields for the preparation and conservation of cellular cultures or parts of cells which are used as such thereafter for the performance of biological test, whereby the cells have to be further sensitized beforehand in relation to a particular hormone or a particular biological or pathological effector.

The cellular cultures or parts of cells prepared with the method according to the invention can be used also in centers not equipped for maintaining cellular cultures for the performance of biological tests, namely the so-called bio-assays.

In particular, the method according to the invention is used to prepare FRTL5 cell cultures, that is to say cells of rat thyroid, which can be employed for the subsequent monitoring and quantifying of the bioactivity of the TSH (hormone of growth) or of the thyroid-stimulating auto-antibodies (TSab).

BACKGROUND OF THE INVENTION

Biological tests are used at the present times in the medical, clinical and research fields to monitor and quantify the biological activity of activating or inhibiting factors which cannot be otherwise identified and quantified reliably with other laboratory techniques.

To carry out such biological tests, it is necessary to use animals or cellular cultures and, in the latter case, to subject the cells at times to a step of preliminary preparation called the "starvation" or "privation" step, in which the cells are bred in complete absence of a hormone, which is then used as a stimulator to increase the sensitivity of the cells to that hormone.

The cells which have undergone the "starvation" or "privation" step are called "cells in the ready state".

The sensitization is also effective in the same manner as regards pathological stimulators such as the thyroid-stimulating auto-antibodies (TSab).

This "privation" step has a duration which can be varied according to the type of tests and which lasts at least for some days, generally between about 5 and 10 days.

A first method arranges to keep the colonies of cells continually in incubation until the moment of performance of the test.

This method entails a plurality of drawbacks such as the high cost arising from the consumption of the culture medium required for maintaining cells always ready for possible tests, the danger of contamination of the culture medium with a resulting lack of validity of the tests carried out, the need to ensure the maintaining of sterility during the whole period of starvation, the need to change the medium, the maintaining of standard conditions during the whole period and the difficulty of transferring the cultures to a distance.

Moreover, this method of extempore production of the cultures when required does not ensure a production of homogeneous and reproducible cultures with the consequence that the results achieved with cultures produced at different periods and/or at different places cannot always be completely compared to each other.

So as to avoid some of these problems, a method is sometimes used whereby the cultures are frozen before the starvation step.

This second method, on the one hand, reduces the costs of the additives required during the cultivation of the cultures but, on the other hand, does not solve the problems linked to the long times of the starvation period and to the standardization of the final product.

In particular, this method consists in freezing at a temperature of at least −80° C., but typically at temperatures of about −196° C. in liquid nitrogen, the cells which have to be used.

These frozen cells, so as to be used, have to be subjected to thawing and to a successive period of recovery during which the cells are deposited on, and possible adhere to, the plastic bottom of the container and then undergo the starvation step.

This period of recovery may last even for some days, which have to be added to the time of the starvation step and which prolong further the times of preparation of the cellular cultures.

Moreover, this method does not make possible a standardization of the samples that ensures the complete reproducibility of the experiments, and therefore restricts the validity of the latter.

Furthermore, another very important problem which has still not been overcome arises from the fact that up to the present time only the laboratories duly equipped and expert in cellular cultures are able to carry out biological tests on cells in vitro, namely the so-called bio-assays, since only those laboratories are able to produce and to keep alive the cellular cultures required for carrying out such tests.

The present applicants have studied, tested and obtained this invention so as to overcome the shortcomings of the state of the art and to achieve further advantages.

SUMMARY OF THE INVENTION

The purpose of this invention is to provide a method for the preparation and conservation of cellular cultures or parts of cells in the ready state for biological tests which can be carried out in very short times.

A further purpose of the invention is, for the first time, to enable these test to be carried out above all by users who are not equipped for, and/or are not capable of, ensuring the maintaining of cellular cultures or the production of part of the latter.

The method according to the invention therefore makes it possible to provide biological material prepared for the performance of bio-assays in a state equivalent to the kits normally and widely used nowadays for clinical biochemistry and for radio-immunology of the traditional technique.

A further purpose of the invention is to provide a method for the preparation of cellular cultures or parts of cells which have been standardized and which make possible quality controls suitable to ensure the sterility and quality of the cultures produced.

Moreover, the method according to the invention makes possible the production of great quantities of cellular cultures or parts of cells which possess the same characteristics and which can therefore be used for carrying out experiments at different times and/or places and for comparing the results obtained.

The method according to the invention also makes possible the production, even on a large scale, of cellular cultures or parts of cells possessing the required characteristics at considerably lower costs owing to the reduced number of handlings and containers required per unit of product and owing to the reduced times of performance of the method.

In the method according to the invention a plurality of cellular populations produced, as previously described, by continually incubating cells such as FRTL-5 cells which have a thyroid stimulating hormone (TSH) receptor are subjected all together to the starvation step for the period necessary for increasing the sensitization of those populations.

Next, the various cellular populations or populations of parts of cells, after being purified, undergo a conservation step and are then supplied in the ready state for biological tests without any significant loss of vitality or function.

The conservation step can be carried out with different processes, depending on the duration of the time during which these cellular cultures or parts of cells have to be conserved.

In order to ensure that the starvation and conservation steps have been correctly carried out and that the cellular cultures or parts of cells subjected to the conservation process meet the desired characteristics, it is possible to carry out an analysis on an aliquot part of those cellular cultures or parts of cells.

This method ensures that all the cellular cultures or parts of cells obtained with the same starvation treatment and the same conservation process possess the same characteristics.

In particular, this method enables a plurality of cellular cultures or parts of cells to be made available which have the same identical characteristics and can therefore be used by a plurality of laboratories, even though not equipped for cellular cultures, in carrying out the biological tests and in comparing thereafter the results obtained.

A first conservation process provides for the freezing at a temperature of about −80° C. or even at lower temperatures and for the storage at the same place while waiting to be used or else for the despatch and subsequent use of the cultures elsewhere by their recipient.

The recipient is typically an analysis laboratory or a research laboratory or a medical office, even if not particularly equipped for, and/or not particularly expert in, cellular cultures.

The cellular cultures or parts of cells at the time of their use are thawed and after a period for recovery, preferably of about some hours at the most, are used for the biological test.

As noted above, according to practices at the present time, cells which have been prepared and frozen before sensitization, so as to be used, have to be subjected to thawing and to a period of recovery during which the cells are deposited on and adhere to the plastic bottom of the container, and then undergo the starvation step for increasing sensitivity.

The present applicants have discovered that preparing and starving the cells for increasing sensitivity during which the cells are deposited on and adhere to the plastic bottom of the containers, and freezing/thawing of the containers of sensitized cultured cells when the cells are adhered to the bottom of the containers after the starvation step has no effect on the sensitiveness and reproducibility of those sensitized cultured cells if they are used preferably within some hours of their thawing.

A second method of conservation provides for the addition of suitable additives to the culture medium.

The cellular cultures thus produced are then sealed and stored for some weeks in a state of apparent biological "stasis" at temperatures the same as the incubation temperatures, generally between 0° C. and +37° C., but advantageously at about +4° C., according to the traditional techniques of the cellular cultures and in conditions suitable to achieve an excellent vitality of the "static" cells These "static" cells, or cells in a state of apparent biological "stasis", are revitalised thereafter by carrying out a change of medium at a suitable moment and by then re-exposing the cells to the classic and well-known fresh culture medium and are incubated to await the biological test to be performed immediately or within a pre-set period of time.

During the period of stasis the cellular cultures can be sealed and thus preserved in the dark under controlled and constant conditions of temperature, pressure and atmosphere.

The constant nature of the atmospheric composition is possibly ensured by hermetic sealing of the containers holding the cellular cultures.

During this storage the cellular cultures in the ready and static state can be transferred to a distance into the premises of the final user for the performance of experiments at different times and/or places and for comparison of the results obtained.

According to a variant, after the starvation step the cellular cultures or parts of cells in the ready state undergo a step of cellular fractionation and partial purification so as to obtain residual parts of cells in the ready state.

These residual parts of cells in the ready state provide the advantage of facilitating their conservation and use.

In particular, these residual parts of cells in the ready state can be subjected to a treatment of lyophilisation and then be stored at the ambient temperature or can be frozen and conserved at temperatures of about −20° C. or at lower temperatures.

BRIEF DESCRIPTION OF THE DRAWING

The attached FIG. 1 is given as a non-restrictive example and shows with a block diagram some preferred solutions of the invention.

DESCRIPTION OF THE DRAWING

The reference number 10 in the attached FIG. 1 denotes generally a method for the preparation and conservation of cellular cultures or parts of cells in the ready state for biological tests according to the invention.

In this case, the method 10 concerns the preparation of cells of the rat thyroid FRTL5, the cells being sensitized at the same time to the TSH hormone and to the thyroid-stimulating auto-antibodies TSab.

The cellular cultures 11 are subjected to a step of starvation or privation 12, in which they are bred in a medium devoid of TSH for a period of time between 7 and 10 days so as to be further sensitized to the TSH hormone and to the TSab.

Next, the cellular cultures or parts of cells in the ready state 11a undergo a conservation process 24 which, depending on the length of the time of conservation desired, may be carried out according to various techniques.

In a first formulation of the invention the conservation process 24 is carried out by subjecting the cellular cultures or parts of cells in the ready state 11a to a step of freezing 13 at a temperature of about −80° C., which does not change their characteristics in any way, in order to obtain cellular cultures or parts of cells in the ready state and frozen 11b.

Next, the cellular cultures or parts of cells in the ready state and frozen 11b are stored and kept in stock 14 until the time of their use.

The cellular cultures or parts of cells in the ready state and frozen 11b can also be despatched and stored, always in the ready state, at the premises of the final user.

So as to control the correct performance of the starvation step 12 and freezing step 13 and to check the quality and characteristics of the cellular cultures or parts of cells in the ready state and frozen 11b, it is possible to carry out possible analyses 15 on a sample of the cellular cultures or parts of cells in the ready state and frozen 11b.

In this way there is available a great quantity of cellular cultures or parts of cells in the ready state and frozen 11b which possess the same characteristics and are ready for use.

To perform the biological tests 18 it is enough to subject the cellular cultures or parts of cells in the ready state and frozen 11b to a thawing step 16 and to a subsequent recovery step 17, which lasts for about 2 hours, thus obtaining cellular cultures or parts of cells in the ready state and thawed 11c.

Thus, cellular cultures or parts of cells in the ready state and thawed 11c which have the same characteristics can be employed both for carrying out the same tests 18 in different laboratories or else different tests 18 on equivalent cellular cultures or parts of cells in the ready state and thawed 11c.

Before the performance of the biological test 18 or at the same time thereas 18, the cellular cultures or parts of cells in the ready state and thawed 11c can be subjected to a further step of quality analysis 115 so as to ensure the reliability of the results of the biological test 18.

According to a variant the cellular cultures or parts of cells in the ready state 11a after the starvation step 12 can undergo a procedure of cellular fractionation or of partial purification 19 of some of their components so as to obtain residual parts of cells 20 which are used in the successive handlings and dosages.

In particular, residual parts of cells 20 obtained downstream of the procedure of cellular fractionation and partial purification 19 can be stored more easily.

In particular, these residual parts of cells 20 can be subjected to a step of conservation 24 by means of lyophilisation 21 and be successively maintained at the ambient temperature or else by being frozen 113 at a temperature of about −20° C.

According to another variant, the conservation 24 of the cellular cultures in the ready state 11a is obtained by subjecting them to a step of "stasis" 22 after they have been possibly treated also with suitable additives.

These "static" cultures 11d are then sealed and stored 14 in environments at a constant temperature, pressure and composition until the moment of their use.

Before being used, these "static" cellular cultures 11d undergo a treatment of "revitalization" 23 by being re-exposed to the classic fresh medium of culture.

With the method 10 according to the invention it is therefore now possible to supply biological material which is ready for use and has a constant and controlled quality even to final users such as analysis or research laboratories and/or medical offices which are not equipped and/or are not expert regarding cellular cultures.

I claim:

1. A method for the preparation of frozen kits of continuously cultured animal cells, wherein said cells have a thyroid stimulating hormone (TSH) receptor, have been standardized to have identical characteristics of hormone-dependent growth and biological responses to activating and inhibiting factors, and are ready-to-use for performing bioassays to monitor and quantify biological activity of said factors within two hours after thawing without loss of vitality, with complete reproducibility, and without need for a user to maintain cell cultures in a tissue culture facility, the method comprising the following steps:

(1) culturing said animal cells having a TSH receptor in continuous culture by contacting them with a culture medium to provide cultured cells which have been standardized to have identical characteristics of hormone-dependent growth and biological responses to activating and inhibiting factors, (2) transferring said standardized cultured cells from the culture medium of step (1) to a container having a plastic bottom and containing hormone-lacking culture medium and culturing said standardized cultured cells in said hormone-lacking medium in the container for a starvation period to increase sensitivity thereof to said hormone, wherein after said starvation period the standardized cultured cells are adhered to the plastic bottom of the container;

(3) freezing the container of sensitized cultured cells from step (2); and (4) storing said frozen kits of sensitized cultured cells provided in step (3).

2. The method according to claim 1, wherein prior to freezing according to step (3), said cultured cells undergo a step of cellular fractionation to provide parts of cells and wherein said cultured cells thereafter comprise said parts of cells.

3. The method according to claim 1, wherein said standardized cultured cells obtained after step (1) undergo a step of cellular fractionation to provide parts of cells and wherein said cultured cells in steps (2)–(4) comprise said parts of cells.

4. The method according to claim 1, wherein said freezing step (3) comprises freezing at a temperature of at least −20 degrees C.

5. The method according to claim 1, wherein said factors comprise TSH and TSH receptor autoantibodies.

6. The method according to claim 1, wherein the freezing step (3) comprises freezing at a temperature of at least −80 degrees C.

7. The method according to claim 1 wherein said animal cells are rat thyroid (FRTL-5) cells.

* * * * *